United States Patent [19]

Jacob

[11] Patent Number: 4,648,871
[45] Date of Patent: Mar. 10, 1987

[54] SUCTION CATHETER
[75] Inventor: Peter Jacob, Söderfors, Sweden
[73] Assignee: Mediplast AB, Solna, Sweden
[21] Appl. No.: 711,505
[22] PCT Filed: Jun. 14, 1983
[86] PCT No.: PCT/SE83/00245
§ 371 Date: Feb. 14, 1985
§ 102(e) Date: Feb. 14, 1985
[87] PCT Pub. No.: WO85/00016
PCT Pub. Date: Jan. 3, 1985
[51] Int. Cl.[4] .............................................. A61M 37/00
[52] U.S. Cl. ..................................... 604/149; 604/48; 604/902
[58] Field of Search ............... 604/149, 28, 35, 22, 604/30, 49, 118, 119, 48, 45, 268, 264, 280, 27, 902, 280.48; 138/112, 115, 111, 114; 29/447

[56] References Cited

U.S. PATENT DOCUMENTS

| 2,912,981 | 11/1959 | Keough | 604/98 |
|---|---|---|---|
| 3,416,532 | 12/1968 | Grossman | 604/45 |
| 3,630,206 | 2/1971 | Gingold | 128/349 B |
| 3,961,853 | 6/1976 | Grimpe | 29/447 |
| 4,222,384 | 9/1980 | Birtwell | 604/103 |
| 4,248,234 | 2/1981 | Assenza et al. | 128/348 |
| 4,382,442 | 5/1983 | Jones | 604/28 |

FOREIGN PATENT DOCUMENTS

| 0145505 | 6/1985 | European Pat. Off. | 604/264 |
|---|---|---|---|
| 330182 | 10/1935 | Italy | 138/115 |
| 83/02900 | 9/1983 | PCT Int'l Appl. | 604/119 |
| 391279 | 2/1977 | Sweden . | |

Primary Examiner—C. Fred Rosenbaum
Assistant Examiner—J. L. Kruter
Attorney, Agent, or Firm—Cushman, Darby & Cushman

[57] ABSTRACT

A suction catheter for sucking body fluids at surgical operations. The catheter comprises an inner and an outer tube manufactured through a coextruding procedure and which form an integrated unit. The outside of the inner tube and/or the inside of the outer tube is provided with longitudinal profilings, which form channels between the inner and outer tube. The channels communicate with the ambient air and provide an air supply to the suction channel when the catheter opening is stopped up.

3 Claims, 3 Drawing Figures

SUCTION CATHETER

The present invention refers to a suction catheter mainly intended for suction of body fluids, e.g. at surgical operations, and which is connectible to a suction means and which comprises an inner and an outer tube forming an integrated unit, wherein on the outside of the inner tube and/or on the inside of the outer tube profilings are provided forming longitudinal channels between the inner and outer tube.

BACKGROUND OF THE INVENTION

In order to prevent that sensible tissues get stuck a good air supply must be provided to the suction orifice at the catheter tip. This has hitherto been a problem and also difficult to combine with the demand that the catheter should be easy and cheap to manufacture. This demand is important as the catheter is a throw-away article.

In a previously known suction catheter of this kind the air supply is provided by a separate ventilation tube fixed on the outside of the catheter and wherein the end of the ventilation tube is passed through an opening in the catheter close to the tip thereof. The manufacture of such a suction catheter is complicated and involves several manual working moments raising the costs.

THE OBJECT AND MOST IMPORTANT FEATURES OF THE INVENTION

The object of the present invention is to provide a suction catheter of the kind stated above and which on one hand provides a good air supply to the suction orifice and by that prevents the tissues to stick thereto and on the other hand is simple and cheap to manufacture.

This has according to the invention been achieved by the fact that said channels communicate with the ambient air and end at or near to the tip of the catheter, where they are arranged to communicate with the suction channel, i.e. the interior of the catheter connected to the suction means.

BRIEF DESCRIPTION OF THE DRAWINGS

The invention will now be described in detail with reference to a pair of embodiments shown in the accompanying drawings.

DESCRIPTION OF EMBODIMENTS

Figure 3:
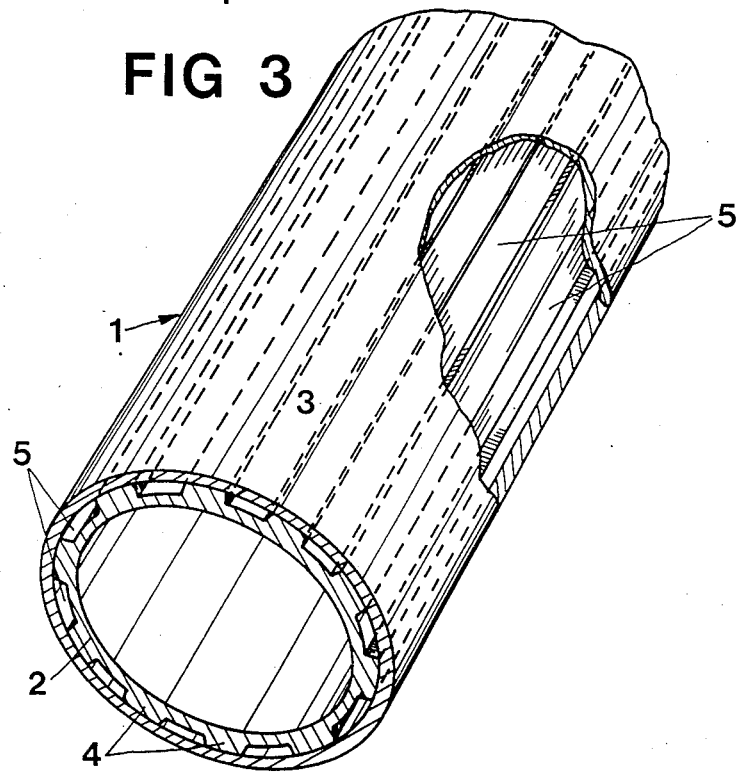
FIG. 3 is a partly broken perspective view of a suction catheter.

The suction catheter 1 comprises an inner and an outer tube 2 and 3 of plastic material manufactured through a coextruding procedure, which means that the outer tube 3 is extruded on the outside of the previously manufactured inner tube 2 and forming an integrated unit therewith. The outside of the inner tube 2 is provided with longitudinal profilings in the form of ridges 4 and grooves 5 (FIG. 3), at which longitudinal channels 5 are formed between the inner and outer tube. Alternatively the inside of the outer tube 3 can of course be provided with such profilings, while the inner tube is even. The interior of the inner tube 2 makes the suction channel 6 and is connected to a suction means (not shown).

Figure 1:
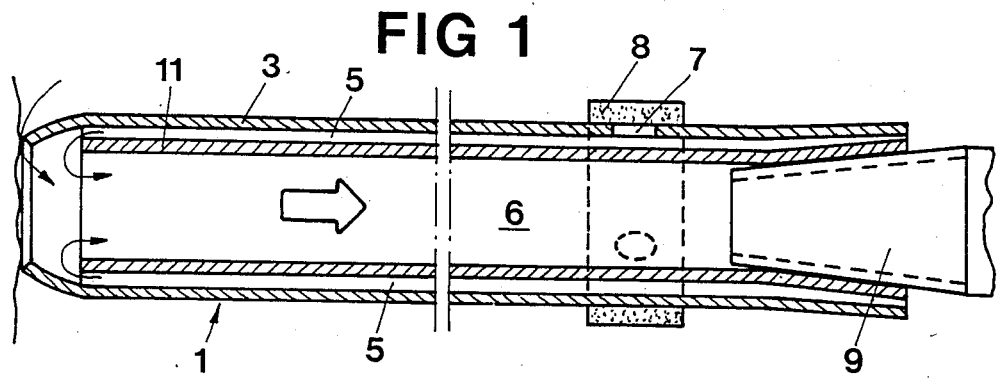
FIG. 1 shown on an enlarged scale a longitudinal section through an embodiment of a suction catheter according to the invention.
Figure 2:
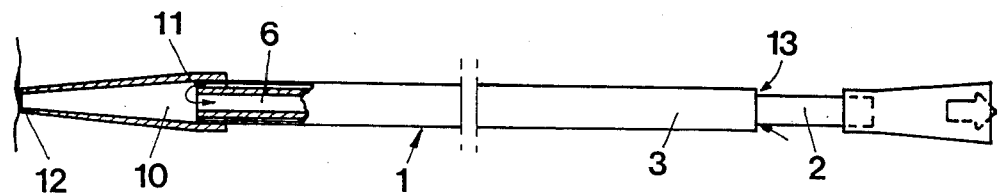
FIG. 2 is a corresponding section through a somewhat modified embodiment.

The channels 5 provide the air supply to the suction channel 6 and communicate with the ambient air e.g. through a radial opening 7 in the outer tube 3 (FIG. 1). The opening 7 is preferably covered by a sterile filter 8. The channels 5 are in this case closed at the rear end of the catheter facing the suction means, e.g. by a conical connection piece 9 inserted into the rear end of the catheter or by a conical connection sleeve attached to the tubes. Alternatively the outer tube 3 can, as is shown in FIG. 2, end a short distance before the rear end of the inner tube 2 so that the channels 5 have an orifice, where a sterile filter can be attached if desired. In the embodiment shown the catheter is at its front end provided with a suction nozzle 10 with such a length that the inner orifices of the channels 5 are located at a considerable distance from the orifice 12 of the nozzle 10. By that the air passing through the outer orifice 13 of the channels 5 needs not to be filtered, as it will not come into contact with the suction object.

The outer tube 3 is preferably made of a material with a higher shrinkability than the inner tube 2, so that the two tubes after cooling form an integrated unit.

If it is desired that the end of the catheter is rounded, as is shown in FIG. 1, the outer tube is manufactured with a length exceeding that of the inner tube. At a heat treatment of this end portion the outer tube 3 will shrink more than the inner tube 2, so that the projecting end of the outer tube is bent in before the edge of the inner tube and forms a rounded end of the catheter. This shape of the catheter tip has the effect that stopping up of the air channels 5 at the catheter tip is obstructed, at the same time as the rounded end facilitates the insertion of the catheter.

Another possibility to achieve the same effect is to make the inner tube of a material which when heated shrinks more in the longitudinal direction than the outer tube. The coextruded tube can then be cut plane, so that the inner and outer tubes are equal long. When shaping the catheter tip by heating it the inner tube will shrink more in the longitudinal direction than the outer tube, so that the desired difference in length occur.

In such cases where a closed rounded catheter tip is desired the open end is heat-sealed by bringing the tube material to float. One or more suction ports are made on the side of the catheter, said ports extending through both tubes.

When the suction catheter is used e.g. for sucking fluids at surgical operations it is connected to a suction means and fluids are sucked through the suction channel 6. When the catheter opening is stopped up air is sucked through the air channels 5, at which it is effectively prevented that the catheter gets stuck.

The invention is of course not limited to the embodiments shown but can be varied within the scope of the accompanying claims.

I claim:

1. A suction catheter for the suction of body fluid adapted to be connected to a suction means, said catheter comprising:

an outer tube;
an inner tube disposed within said outer tube and forming an integrated unit therewith, said inner tube further comprising ridges disposed around the outside of said inner tube, said ridges contacting said outer tube thereby defining air channels between said inner and outer tubes;

wherein said outer tube is made of a material with a higher shrinkability than the inner tube, and wherein said outer tube is longer than said inner tube such that the portion of said outer tube which exceeds the length of the inner tube slightly tapers so that communication between said air channels and a suction channel within said inner tube is maintained.

2. A suction catheter for the suction of body fluid adapted to be connected to a suction means, said catheter comprising:

an outer tube;

an inner tube disposed within said outer tube and forming an integrated unit therewith, said inner tube further comprising ridges disposed around the outside of said inner tube, said ridges contacting said outer tube thereby defining air channels between said inner and outer tubes;

wherein said inner tube is made of a material which when heated shrinks more than the outer tube; and wherein said outer tube is longer than said inner tube such that the portion of said outer tube which exceeds the length of the inner tube and slightly tapers so that communication between said air channels and a suction channel within said inner tube is maintained.

3. A suction catheter for the suction of body fluid adapted to be connected to a suction means, said catheter comprising:

an outer tube;

an inner tube disposed within said outer tube and forming an integrated unit therewith, said inner tube further comprising ridges disposed around the outside of said inner tube, said ridges contacting said outer tube thereby defining air channels between said inner and outer tubes; and a suction nozzle;

wherein said outer tube is made of a material which is of a higher shrinkability than said inner tube, and wherein said suction nozzle is disposed so as to surround said outer tube and extend from the end of said catheter which is to be used for suction of body fluid.

* * * * *